(12) United States Patent
Langer et al.

(10) Patent No.: US 7,094,923 B2
(45) Date of Patent: *Aug. 22, 2006

(54) METHOD FOR PRODUCING SUBSTITUTED NITRO BENZOIC ACIDS BY OXIDATION OF CORRESPONDING NITRO TOLUENES, NITRO BENZYL ALCOHOLS, ESTERS AND/OR ETHERS

(75) Inventors: Reinhard Langer, Tönisvorst (DE); Lars Rodefeld, Leverkusen (DE); Karl Heinz Neumann, Augustin (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/083,746

(22) Filed: Mar. 17, 2005

(65) Prior Publication Data

US 2005/0165247 A1    Jul. 28, 2005

Related U.S. Application Data

(62) Division of application No. 10/257,062, filed as application No. PCT/EP01/03667 on Mar. 30, 2001.

(30) Foreign Application Priority Data

Apr. 12, 2000    (DE)  ................................ 100 18 048

(51) Int. Cl.
*C07C 309/00*    (2006.01)
*C07C 51/16*    (2006.01)
*C07C 51/255*    (2006.01)
*C07C 51/23*    (2006.01)
*C07C 51/15*    (2006.01)

(52) U.S. Cl. ........................ 562/57; 562/410; 562/434; 562/438

(58) Field of Classification Search ...................... None
See application file for complete search history.

(56) References Cited

FOREIGN PATENT DOCUMENTS

| | | | |
|---|---|---|---|
| CN | 1104626 A | * | 7/1993 |
| DE | 197 49 723 | | 5/1999 |
| DE | 19 927 408 | | 12/2000 |
| EP | 0 916 653 | | 5/1999 |
| GB | 705 195 | | 3/1954 |
| GB | 960 246 | | 6/1964 |
| GB | 1 068 535 | | 5/1967 |
| HU | 214 022 B | * | 4/1997 |
| SE | 140411 | * | 10/1950 |
| SU | 1421733 A1 | * | 9/1988 |

OTHER PUBLICATIONS

Bengtsson, "Continuous High-Pressure Oxidation with Nitric Acid in a Tubular Converter" IVA (The Royal Swedish Academy of Engingeering Sciences), vol. 25(3), pp. 121-124 (1954).*
Faith, Keyes and Clark's Industrial Chemicals 4th Ed, pp. 563-570, John Wiley & Sons, Inc. © 1975.*
Yi et al, "Synthesis of p-Nitrobenzoic Acid" Guangzhou Huagong, vol. 26(2), pp. 9-10 (1988). With English Translation.*
Srinivasan and Chandalia, "Oxidation of p-Nitrotoluene to p-Nitrobenzoic Acid by Nitric Acid" Indian Journal of Technology, vol. 9(7), pp. 274-275 (1971).*
Dolmatov et al, "Preparation of m-Nitrobenzoic Acid via Oxidation of m-Nitrotoluene with Diluted Nitric Acid under Pressure" Khimiko-Farmatsevticheskii Zhurnal, vol. 24(1), pp. 67-69 (1990). With English Translation.*
Chemiker-Zeitung, 104, Nr. 12, (month unavailable) 1980, pp. 349-351, Von Erik Bengtsson und Boris Holm, "Oxidation mit Salpetersäure".

* cited by examiner

*Primary Examiner*—James O. Wilson
*Assistant Examiner*—Zachary C. Tucker
(74) *Attorney, Agent, or Firm*—Jennifer R. Seng

(57) ABSTRACT

The present invention relates to the preparation of nitrobenzoic acids by oxidizing particular nitrotoluenes, nitrobenzyl alcohols, esters and/or ethers in the presence of nitric acid at elevated temperature and elevated pressure. It has been found that the particular nitrotoluenes, nitrobenzyl alcohols, esters and/or ethers may be oxidized particularly reliably and in high yields using nitric acid to the benzoic acid derivatives when they are metered into the nitric acid.

7 Claims, No Drawings

METHOD FOR PRODUCING SUBSTITUTED NITRO BENZOIC ACIDS BY OXIDATION OF CORRESPONDING NITRO TOLUENES, NITRO BENZYL ALCOHOLS, ESTERS AND/OR ETHERS

This application is a Divisional of Ser. No. 10/257,062, flied Oct. 8, 2002, now U.S. Pat. No. 6,900,349 which is a 371 of PCT/EP01/03667 filed on Mar. 30, 2001.

The present invention relates to a process for preparing specifically substituted nitrobenzoic acids by oxidizing the corresponding nitrotoluenes, nitrobenzyl alcohols, and esters and/or ethers thereof using nitric acid.

Substituted nitrobenzoic acids are interesting intermediates for active pharmaceutical and agrochemical ingredients.

Nitrotoluenes having additional electron-withdrawing, especially oxygen-containing, substituents are compounds whose autothermal decomposition leads to a considerable release of energy. In view of the high reaction temperatures which are required at the same time, the oxidation of such compounds is difficult to realize from a safety point of view. When carried out on an industrial scale, it requires considerable control, and special measures have to be taken to minimize the safety risk.

Commercially, electron-deficient nitrotoluenes are oxidized using nitric acid in continuously operated delay tubes, as described in the Chemiker-Zeitung 104 (1980), p. 349–351. A mixture of nitric acid and toluene is preheated and pumped under high pressure through a vertical reactor tube. It is pointed out that there is always a risk of an explosion here, for which reason a protective wall is always constructed between the reactor and the control room and the reaction may only be carried out by remote control from the control room.

A further disadvantage of such a continuous process is that start-up and shut-down conditions may lead to off-spec material, which is problematic especially in products having relatively low tonnages.

GB-A-705 195 describes the oxidation of toluenesulfonic acids and nitrotoluenesulfonic acids using nitric acid at 120–300° C. in an autoclave, optionally with the aid of oxygen, nitrous gases, metal nitrates or metal nitrites. The components are added together and the pressure reactor is heated until a strongly exothermic reaction commences. Both continuous and semicontinuous performance of the reaction are described. In the semicontinuous procedure, the oxidizing agent is metered into the (nitro)toluenesulfonic acid.

DE-A-197 49 723 describes the preparation of 4-nitro-2-sulfonylbenzoic acid by oxidizing 4-nitrotoluene-2-sulfonic acid at 120–170° C. and a pressure of up to 12 bar by initially charging the toluene dissolved in water and metering in the nitric acid. Explicit reference is made to the safety aspects of this reaction. In addition, the yields of 75–85% achievable in this process are unsatisfactory with regard to industrial preparation.

The object of the present invention is accordingly to provide an oxidation process by which substituted nitrobenzoic acids may be obtained without safety risk and in high reproducible yields even in small tonnages.

Surprisingly, it has been found that this object may be achieved by a semibatch process involving initially charging the oxidizing agent and then metering in the reactant in the form of a nitrotoluene, nitrobenzyl alcohol, ester and/or ether at elevated temperature and elevated pressure.

The invention accordingly provides a process for preparing nitrobenzoic acids of the general formula (I)

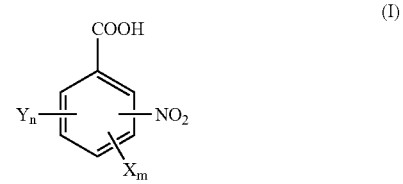

where
  each X is independently nitro, cyano, sulfonyl, carboxyl, carbonylphenyl, trifluoromethyl or trichloromethyl,
  each Y is independently phenyl, fluorine, chlorine, bromine or iodine and the phenyl radical may in turn be substituted by up to 3 X and/or Y radicals other than hydrogen,
  m has the value 0, 1, 2 or 3 and
  n has the value 0, 1, 2 or 3,
  and the sum of m and n has the value 0, 1, 2, 3 or 4,
  from compounds of the general formula (II)

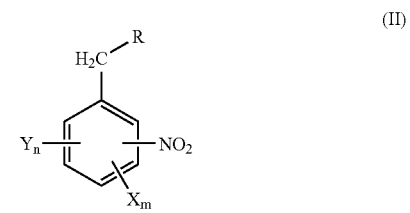

where
  X, Y, m, n and also the sum of n and m are each as defined above for the general formula (I) and
  R is H or an OR' radical and
  R' is H, straight-chain or branched $C_1$–$C_{10}$-alkyl or straight-chain or branched $C_1$–$C_{10}$-carbonylalkyl or R' is a radical of the general formula (II)

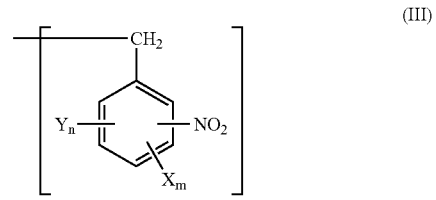

or a radical of the general formula (IV),

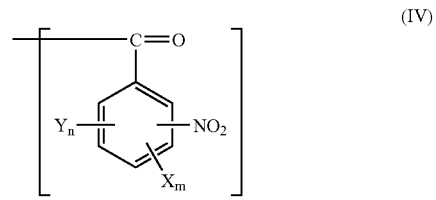

where X, Y, n, m and also the sum of n and m are each as defined for the general formula (I), characterized in that a mixture of nitric acid and water is heated at a pressure in the range of 2–20 bar at temperatures in the range of 100–220° C. and the compound of the general formula (II) is metered into this heated mixture of nitric acid and water, although compounds of the general formula (II) exclude 2-halo-6-nitrobenzyl alcohols, esters and ethers of the general formula (V) and

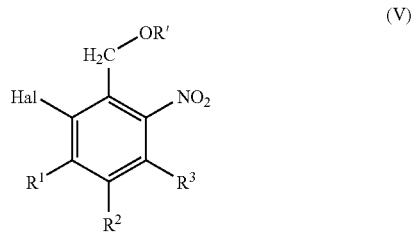

(V)

where

R' is as defined for the general formula (II), $R^1$, $R^2$ and $R^3$ are each independently H, fluorine, chlorine, bromine, nitro or carboxyl and Hal is fluorine, chlorine or bromine.

A decisive factor in the process according to the invention is the mixing of the reactant and the nitric acid in such a manner that the nitric acid is initially charged and heated in a mixture with water and the reactant to be oxidized is then metered in. The steady state concentration of the reactant, whose decomposition temperature is frequently close to the range in which the heat development of the desired reaction takes place, is thus maintained at a particularly low level in the reaction mixture. As soon as the reactant reaches the nitric acid reaction mixture, it reacts immediately with the nitric acid to give an unreactive product. The maximum reactant concentrations in the reaction mixture in the process according to the invention are 7% by weight, preferably 6% by weight and in particular 5% by weight. In this manner, the danger potential of the oxidation is quite decisively reduced.

In the general formulae (I) and (II), each X is independently and preferably a sulfonic acid or nitro radical and each Y is independently and preferably fluorine or chlorine. The index n preferably has a value of 0, 1 or 2 and the index m likewise preferably has a value of 0, 1 or 2, and the sum of n and m preferably has the value 1 or 2. Preferably, a hydrogen atom or a fluorine atom, preferably a hydrogen atom, is in one of the o-positions to the group —CH$_2$R to be oxidized.

Preference is given to applying the process according to the invention to those compounds of the general formula (II) which have a marked tendency to thermally decompose. Particular preference is given to using nitrotoluenes and in particular nitrotoluenesulfonic acids as reactants. Very particular preference is given to oxidizing 4-nitrotoluene-2-sulfonic acid to 4-nitro-2-sulfonylbenzoic acid.

The process according to the invention is carried out at a pressure of 2–20 bar, preferably of 4–15 bar, more preferably of 6–12 bar and in particular of 10–12 bar. Since nitrogen oxides are released in the course of the reaction, it is sensible to control the pressure via a pressure-retaining valve and to allow the nitrogen oxides to escape to the required extent.

The temperature at which the process according to the invention is carried out is in the range of 100–220° C., preferably of 120–200° C. and more preferably of 140–180° C.

The reaction is carried out using an initial charge of 10–90%, and preferably 20–65%, nitric acid.

The molar ratio of the compound of the general formula (II) to nitric acid is in the range of (2–20):1, preferably in the range of (3–10):1 and more preferably in the range of (4–8):1.

The process according to the invention is customarily carried out in such a manner that the nitric acid is initially charged into a pressure reactor and heated. The reactant solution or melt is then metered in within 1–48, preferably 2–24 and more preferably 4–12, hours. The completed metering in is optionally followed by a certain continued reaction time at the reaction temperature for the purposes of completing the conversion. This continued reaction time is customarily in the range of 1–15 hours and preferably in the range of 3–8 hours.

After the end of the oxidation and expiry of any continued stirring time, the reaction mixture may be cooled, the reaction vessel depressurized and the remaining nitrogen oxides blown out, for example using nitrogen.

The nitrosulfonylbenzoic acids of the general formula (I) prepared according to the invention may be isolated, for example, by adding an aqueous, preferably saturated, potassium chloride solution and filtering off the monohydrate of the potassium salt of nitrosulfonylbenzoic acid which then precipitates. After it has dried, a product is generally obtained which has a purity of over 95% by weight (determined by HPLC).

The potassium salt may also be precipitated in such a manner that an aqueous potassium hydroxide solution, for example having a concentration of 30–50% by weight, is added until the pH is in the range of, for example, 0.5–2.5. The majority of the nitrosulfonylbenzoic acid then precipitates as the potassium salt. If necessary, the precipitation may be completed by adding an aqueous, preferably saturated, potassium chloride solution.

Other methods for isolating the benzoic acid derivatives of the general formula (I) obtained by oxidation are generally known to those skilled in the art.

In a particular embodiment of the process according to the invention, 10–90%, preferably 20–50%, of the nitric acid to be used is initially charged and heated, and the reactant and remaining nitric acid are then metered into the reactor simultaneously but separately.

It may also be advantageous to add substances to the initially charged nitric acid which release or contain NO$_x$, for example alkali metal or alkaline earth metal nitrites, nitrous acid or concentrated red-brown nitric acid. This allows the required reaction temperature to be reduced and the danger potential to be thereby further reduced.

The reactant of the general formula (II) may be metered into the nitric acid reaction mixture either as a melt or dissolved in a solvent. Useful solvents include liquids which are barely oxidizable if at all and are inert toward nitric acid under the given reaction conditions, preferably water, nitrobenzene, 1,2,4-trichlorobenzene or methylene chloride. Low-boiling solvents such as methylene chloride are transported out of the reactor with the NO$_x$ stream.

In the process according to the invention, preference is given to metering the compounds of the general formula (II) and in particular the nitrosulfonyltoluenes into the nitric acid as a 20–70%, preferably 30–55%, aqueous solution.

DTA investigations of the reaction mixtures of the process according to the invention for oxidizing the nitro compounds of the general formula (II) gave no grounds for any potential danger to safety; in the case of the present reaction mixtures, insignificant exothermic reactions only take place at temperatures in the range of 260–370° C. This is a significant advantage in terms of safety over the nearest prior art process having reverse operation, i.e. the initial charging of, for example, 4-nitrotoluenesulfonic acid and subsequent metering in of nitric acid. DTA investigations of such reaction mixtures show that the first exothermic decomposition reactions commence at only 175° C. and that further decomposition proceeds above 250° C. to a quite massive extent.

EXAMPLES

Example 1 (Comparative)

In a 1 l tantalum autoclave equipped with a stirrer, reflux condenser and a pressure-retaining valve set to 5 bar, 108.6 g of water-damp 4-nitrotoluene-2-sulfonic acid (0.39 mol) are suspended in 120 g of water and heated to 140° C. A pressure of about 3.6 bar builds up. Once this temperature is attained, 180 g of 70% by weight nitric acid are pumped into the autoclave within 5 h. Owing to the development of $NO_x$, the pressure rises to the predetermined 5 bar, and when this pressure is exceeded, the nitrogen oxides formed are blown off. After the end of the nitric acid metering, stirring is continued at 140° C. for 12 h. In the last hours of the continued stirring time, the pressure falls again to below 5 bar and the offgas stream ceases. After the autoclave has been cooled to room temperature, it is depressurized and the remaining nitrogen oxides are purged out using nitrogen. The autoclave contents are transferred to a flask equipped with a stirrer, and 150 g of a cold saturated aqueous KCl solution are added. The 4-nitro-2-sulfonylbenzoic acid precipitates as the potassium salt, is filtered off, washed with cold water and dried in a drying cabinet.

96 g of the monohydrate of the potassium salt of 4-nitro-2-sulfonylbenzoic acid having a purity of 97% (HPLC) are isolated which corresponds to a yield of 78.5%, based on the 4-nitrotoluene-2-sulfonic acid used.

In table 1, the reactant concentration in the reaction mixture is presented as a function of the reaction time.

Example 2 (Comparative)

In the apparatus described in example 1, 108.6 g of water-damp 4-nitrotoluene-2-sulfonic acid (0.39 mol) are suspended in 120 g of water and heated to 160° C. A pressure of about 6.1 bar builds up. Once this temperature is attained, 180 g of 70% by weight nitric acid are pumped into the autoclave within 4 h. Owing to the development of $NO_x$, the pressure rises to the predetermined 9 bar, and when this pressure is exceeded, the nitrogen oxides formed are blown off. After the end of the nitric acid metering, stirring is continued at 160° C. for 1 h. In the last hours of the continued stirring time, the pressure falls again to below 9 bar and the offgas stream ceases.

The work-up is effected in a similar manner to example 1, and 92.4 g of the monohydrate of the potassium salt of 4-nitro-2-sulfonylbenzoic acid having a purity of 97% (HPLC) are isolated which corresponds to a yield of 75.6%, based on the 4-nitrotoluene-2-sulfonic acid used.

In table 1, the reaction concentration in the reaction mixture is presented as a function of the reaction time.

Example 3

581.5 g of 65% nitric acid are heated in a steel-enamel autoclave to 160° C. 684.8 g of a 31.7% 4-nitrotoluene-2-sulfonic acid solution are then metered in over 10 hours. The internal pressure is maintained at 12 bar. Stirring is then continued at this temperature for 6 h. The batch is transferred with 150 g of water to a reservoir and 389.5 g of a 50% potassium hydroxide solution are added dropwise at 60° C. over 2 h. After stirring for a further 2 hours, the batch is filtered. The precipitate is then washed twice with half of 150 g of ice-water each time. The product is dried at 50–80° C. and 50–100 mbar to obtain 273.8 g, of product, of which 99.1% is the monopotassium salt of 4-nitro-2-sulfonylbenzoic acid and 0.3% is the reactant, and the total water and potassium nitrate content is about 0.6%. The yield is accordingly 94% of theory, based on the 4-nitrotoluene-2-sulfonic acid used.

In table 1, the reactant concentration in the reaction mixture is presented as a function of the reaction time.

Example 4

581.5 g of 65% nitric acid are heated in a steel-enamel autoclave to 140° C. 684.8 g of a 31.7% 4-nitrotoluene-2-sulfonic acid solution are then metered in over 10 hours. The internal pressure is maintained at 12 bar. Stirring is then continued at this temperature for 6 h.

The work-up of the reaction mixture is effected as described in example 3. A product is obtained which has a residual content of 2% of the potassium salt of 4-nitrotoluene-2-sulfonic acid. The yield of the monopotassium salt of 4-nitro-2-sulfonylbenzoic acid is about 91% of theory, based on the 4-nitrotoluene-2-sulfonic acid used.

In table 1, the reactant concentration in the reactant mixture is presented as a function of the reaction time. The slightly lower temperature than in example 3 leads to steady state concentrations of the reactant of below 5% by weight. This value may be reduced by adding 0.01 mol of sodium nitrite to the nitric acid before the reaction (example 5).

Example 5

581.5 g of 65% nitric acid are admixed with 690 mg (0.01 mol) of sodium nitrite and heated in a steel-enamel autoclave to 140° C. 684.8 g of a 31.7% 4-nitrotoluene-2-sulfonic acid solution are then metered in over 10 hours. The internal pressure is maintained at 12 bar. Stirring is then continued at this temperature for 6 h.

The work-up of the reaction mixture is effected as described in example 3, and a product is obtained which still has a residual content of 0.9% of the potassium salt of 4-nitrotoluene-2-sulfonic acid. The yield of the monopotassium salt of 4-nitro-2-sulfonylbenzoic acid is about 93% of theory, based on the 4-nitrotoluene-2-sulfonic acid used.

In table 1, the reactant concentration in the reaction mixture is presented as a function of the reaction time. The steady state concentrations of the reactant during the reaction do not exceed 3% at any time.

TABLE 1

Reactant concentration in the reaction mixture as a function of the reaction time

| Example | Time [hours] | Reactant content in solution [% by weight] |
|---|---|---|
| 1 (comparative) | 0 | 37 |
|  | 2.5 | 13 |
|  | 5 | 5 |
|  | 17 | 0.7 |
| 2 (comparative) | 0 | 37 |
|  | 2 | 11 |
|  | 4 | 3 |
|  | 5 | 0.8 |
| 3 | 3.3 | 0.48 |
|  | 6.7 | 1.31 |
|  | 10 | 2.11 |
|  | 14 | 0.14 |
| 4 | 2 | 4.65 |
|  | 4 | 3.69 |
|  | 6 | 3 |
|  | 8 | 3.5 |
|  | 10 | 3.6 |
|  | 16 | 0.64 |
| 5 | 2 | 2.62 |
|  | 4 | 2.06 |
|  | 6 | 2.38 |
|  | 8 | 2.55 |
|  | 10 | 2.83 |
|  | 16 | 0.22 |

The invention claimed is:

1. A process for preparing nitrobenzoic acids of the general formula (I)

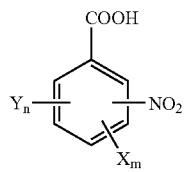
(I)

where
each X is independently nitro, cyano, sulfonyl, carboxyl, carbonylphenyl, trifluoromethyl or trichloromethyl,
each Y is independently phenyl, fluorine, chlorine, bromine or iodine and the phenyl radical, optionally substituted by up to 3 X and/or Y radicals other than hydrogen,
m has the value 0, 1, 2 or 3 and
n has the value 0, 1, 2 or 3,
and the sum of m and n has the value 1, 2, 3 or 4,
from compounds of the general formula (II)

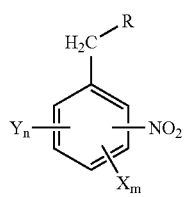
(II)

where
X, Y m, n and also the sum of n and m are each as defined above for the general formula (I) and
R is H or an OR' radical and
R' is H, straight-chain or branched $C_1$–$C_{10}$–alkyl or straight-chain or branched $C_1$–$C_{10}$-carbonylalkyl or R' is a radical of the general formula (III)

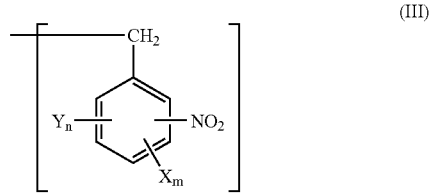
(III)

or a radical of the general formula (IV),

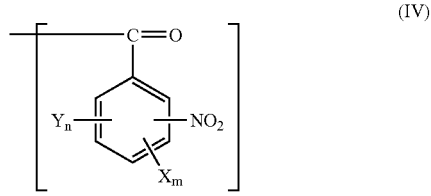
(IV)

where X, Y, n, m, and the sum of n and m are each as defined for the general formula (I),
comprising heating a mixture of nitric acid and water at a pressure in the range of 2–20 bar at temperatures in the range of 100–220° C. and metering the compound of the general formula (II) into the heated mixture of nitric acid and water,
with the proviso that compounds of the general formula (II) exclude 2-halo-6-nitrobenzyl alcohols, esters or ethers of the general formula (V) and

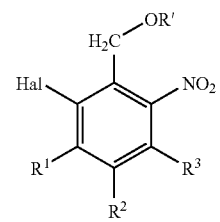
(V)

where
R' is as defined for the general formula (II),
$R^1$, $R^2$ and $R^3$ are each independently H, fluorine, chlorine, bromine, nitro or carboxyl and
Hal is fluorine, chlorine or bromine.

2. The process as claimed in claim 1, wherein each X in the general formulae (I) and (II) is independently a sulfonic acid or nitro radical and each Y is independently fluorine or chlorine.

3. The process as claimed in claim 1, wherein a hydrogen atom or a fluorine atom, is in one of the o-positions to the group —$CH_2R$ to be oxidized.

4. The process as claimed in claim 1, wherein 10–90% nitric acid is initially charged.

5. The process as claimed in claim 1, wherein $NO_x$-releasing substances or NO-containing substances are added to the nitric acid.

6. The process as claimed in claim 1, wherein a hydrogen atom, is in one of the o-positions to the group —$CH_2R$ to be oxidized.

7. The process as claimed in claim 1, wherein 20–65% nitric acid is initially charged.

* * * * *